United States Patent
Baudino

[19]

[11] Patent Number: 5,869,078
[45] Date of Patent: Feb. 9, 1999

[54] IMPLANTABLE VARIABLE PERMEABILITY DRUG INFUSION TECHNIQUES

[75] Inventor: Michael D. Baudino, Coon Rapids, Minn.

[73] Assignee: Medtronic Inc., Minneapolis, Minn.

[21] Appl. No.: 637,439

[22] Filed: Apr. 25, 1996

[51] Int. Cl.⁶ ............................... A61F 2/02; A61K 9/22; A61N 1/18
[52] U.S. Cl. .......................... 424/423; 604/891.1; 607/35
[58] Field of Search ............................. 424/423; 607/35; 604/891.1, 892.1

[56] References Cited

U.S. PATENT DOCUMENTS

| | | |
|---|---|---|
| 4,513,034 | 4/1985 | Sparer et al. . |
| 4,624,847 | 11/1986 | Ayer et al. . |
| 5,314,458 | 5/1994 | Najafi et al. . |
| 5,370,672 | 12/1994 | Fowler et al. . |

*Primary Examiner*—Carlos A. Azpuru
*Attorney, Agent, or Firm*—Banner & Witcoff Ltd.

[57] ABSTRACT

An implantable dispensing device for delivering a treatment agent to a body including a body fluid in which a variable permeability membrane responds to changes in an electromagnetic parameter in order to vary the rate at which a hygroscopic media increases in volume, thereby controlling the rate of delivery of a treatment agent, such as a drug.

24 Claims, 2 Drawing Sheets

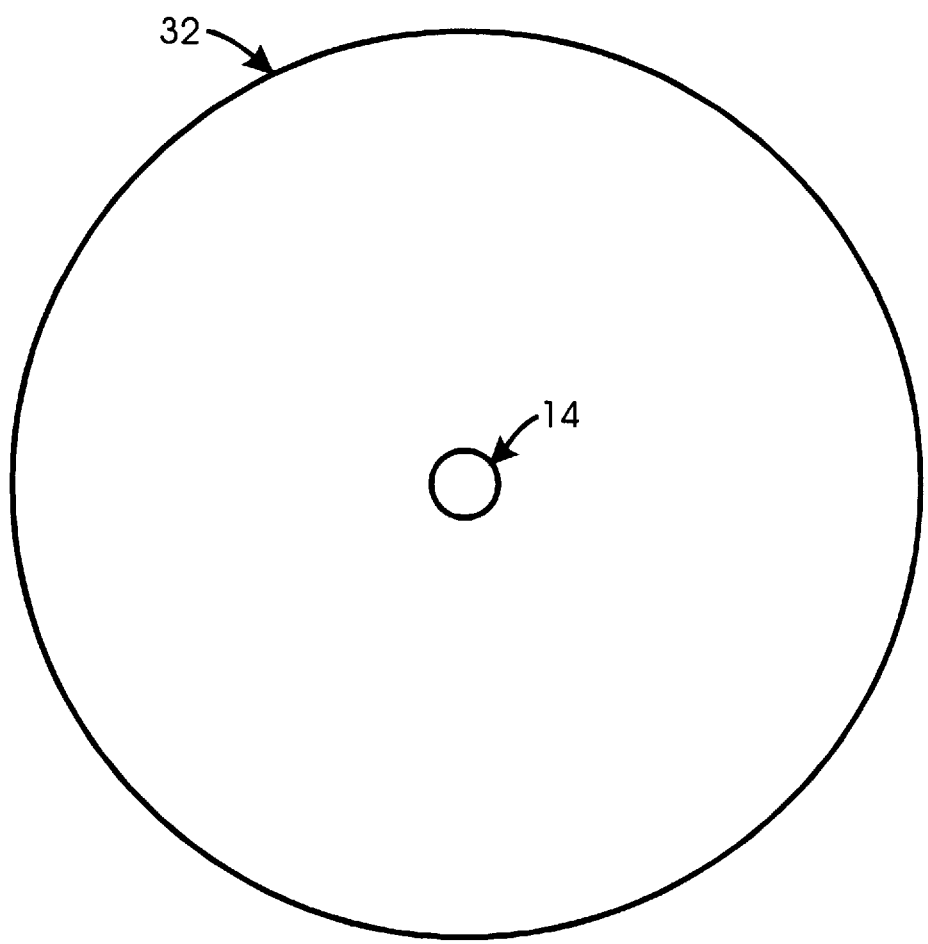

IMPLANTABLE VARIABLE PERMEABILITY DRUG INFUSION TECHNIQUES

BACKGROUND OF THE INVENTION

1. Field of the Invention

This invention relates to implantable drug delivery techniques, and more particularly to such techniques in which fluid from a body is used to provide a force which delivers a treatment agent.

2. Description of Related Art

Drug delivery systems based on osmotic pumps are known and are described, for example, in U.S. Pat. No. 4,624,847 (Ayers et al.), issued Nov. 25, 1986. When using such an osmotic pump, it is impossible to control the rate of hydration of the osmotic medium. In known osmotic pumps, a porous membrane separates a hygroscopic media from body fluids. As the membrane passes water from the body into the pump due to osmosis, the media swells and forces the infusate out of a reservoir. Such an osmotic pump is a passive device that has a fixed infusion rate and no on/off control. This invention addresses the fixed infusion rate problem of known osmotic pumps which limits their therapeutic value.

SUMMARY OF THE INVENTION

The invention useful for dispensing a treatment agent, such as a drug, to a body including a body fluid. A preferred form of dispensing device useful in such an environment includes a first chamber for holding the treatment agent. A conduit is located between the first chamber and the body for delivering the treatment agent to the body. A second chamber holds a hygroscopic media. There is a means for applying pressure to the first chamber due to an increase in volume of the hygroscopic media in the second chamber so that the treatment agent is delivered through the conduit to the body. A variable permeability membrane responds to changes in an electromagnetic parameter for controlling the rate at which the volume of the hygroscopic media is increased. Means also are provided for controlling the value of the electromagnetic parameter, whereby the rate of delivery of the treatment agent is controlled. By using the foregoing techniques, the rate at which a treatment agent can be delivered from an implantable device is made controllable, thereby increasing the therapeutic value of the treatment agent.

BRIEF DESCRIPTION OF THE DRAWINGS

These and other advantages and features will become apparent upon reading the following detailed description and referring to the accompanying drawings in which like numbers refer to like parts throughout and in which:

FIG. 2 is a top plan view the device shown in FIG. 1.

DESCRIPTION OF THE PREFERRED EMBODIMENTS

Figure 1:
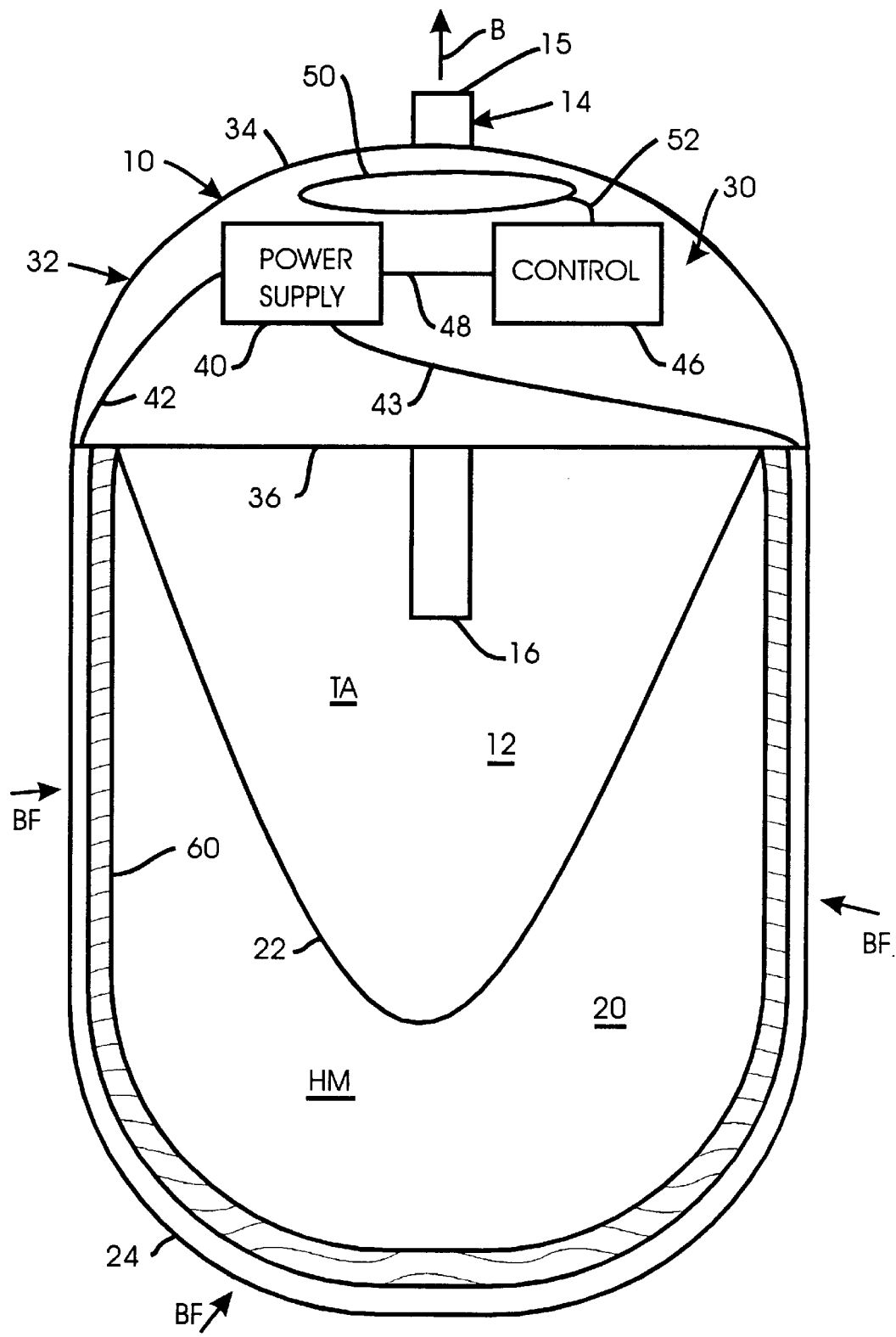
FIG. 1 is a diagrammatic and partially cross-sectional view of a preferred form of implantable dispensing device made in accordance with a preferred practice of the invention.

Referring to FIGS. 1 and 2, a preferred form of implantable device made in accordance with the invention is adapted to be implanted in a body that includes body fluid BF. Device 10 includes a chamber 12 that holds a treatment agent TA, such as a drug, intended to be infused into the body for therapeutic treatment. A conduit 14 enables the delivery of treatment agent TA from reservoir 12 to the body in the direction of arrow B. The conduit comprises a hollow, cylindrical 21 gauge stainless steel tube having an outer end 15 in contact with the body and an inner end 16 in contact with the treatment agent in chamber 12.

Device 10 also includes a chamber 20 for holding a hygroscopic media HM. Such media include a solution of sodium chloride and water or a hydrophilic polymer (e.g., hydrogel) having a composition such that as hydration occurs, the media swells due to osmosis, creating a displacement force that exerts pressure on chamber 12.

Chamber 12 is separated from chamber 20 by a plastic synthetic elastomer impermeable sheet 22 that is deformable due to the increase volume of hygroscopic media HM. When the volume of the hygroscopic media increases, sheet 22 deforms, thereby applying pressure to chamber 12 so that treatment agent TA is delivered from chamber 12 through conduit 14 to the body in the direction of arrow B.

Device 10 also includes a variable permeability membrane 24 that has a generally cylindrical shape. One such membrane suitable for use with the present invention is described in U.S. Pat. No. 4,513,034 (Sparer et al, issued Apr. 23, 1985, "the '034 Patent"). As described in the '034 Patent, membrane 24 comprises a liquid crystalline membrane with a porous structure containing a polymeric liquid crystal which can undergo a phase change. The phase change can be controlled by various electromagnetic parameters, including an electrical field and a magnetic field. The '034 Patent is incorporated by reference.

Referring to FIG. 1, device I 0 includes a control module which is held in a sealed chamber 32 defined by a dome structure 34 and circular disk-shaped flange 36 which seals chamber 32 from chambers 12 and 20. Control module 30 includes a power supply 40 which applies a voltage to membrane 24 through conductors 42 and 43. The voltage supplied by the conductors changes the electric field of membrane 24 in order to adjust the permeability or pore size of the membrane, thereby controlling the rate at which the hygroscopic media HM increase its volume. The rate at which the hygroscopic media increases its volume controls the rate at which treatment agent TA is infused from chamber 12 to the body. Alternatively, the power supply could vary the magnetic field applied to membrane 24. If the pore size of membrane 24 is increased, body fluid BF diffuses from the body to chamber 20 at an increased rate, thereby increasing the rate at which the volume of the hygroscopic media increases.

The value of the voltage applied to conductors 42 and 43 by power supply 40 is determined by the value of a signal transported over a conductor 48 from a control circuit 46. The control circuit receives radio frequency power signals through an antenna lead 52 from a antenna 50 located as shown in control module 30. Antenna 50 receives radio frequency signals from a conventional transmitting antenna located outside the body. Apparatus for transmitting electrical power and data signals to an implanted device are well known, and are described, for example, in U.S. Pat. Nos. 5,314,458 (Najafi, issued May. 24, 1994) and 5,370,672 (Fowler et al., issued Dec. 6, 1994). In a well-known manner, control circuit 46 receives data from the radio frequency signals received by antenna 50 and processes the data in order to determine the proper value of control signal to be transmitted to power supply 40 in order to control the voltage applied to membrane 24.

Device 10 also may include a conventional semipermeable membrane 60 of the type normally supplied with existing osmotic pumps.

Control circuit 46 may be programmed so that membrane 24 operates as an on/off switch to control the delivery of treatment agent TA. In this mode of operation, when a bias is placed on membrane 24, it causes the membrane to open its pores which allows body fluid BF to be passed into the hygroscopic media HM. The influx of body fluid results in infusion of treatment agent TA into the body. Removal of the bias results in a closure of the pores of membrane 24 and a cessation of infusion. Preferably, membrane 24 is bistable, i.e., the membrane requires energy only in order to change the state of its pores from open to closed. However, membrane 24 also may be of the type which requires a continuous bias and offers a continuously variable pore size.

Power for supplying an appropriate electromagnetic parameter to membrane 24 may be supplied from a battery held within power supply 40, or antenna 50 may continuously receive electrical power signals which provide the energy for biasing membrane 24.

Those skilled in the art will recognize that the preferred embodiments may be altered or amended without departing from the true spirit and scope of the invention, as defined in the accompanying claims.

I claim:

1. An implantable dispensing device for delivering a treatment agent to a body including body fluid comprising in combination:

a first chamber for holding said treatment agent;

a conduit between said first chamber and said body;

a second chamber for holding a hygroscopic media;

means for applying pressure to said first chamber due to an increase in volume of said media in said second chamber so that said treatment agent is delivered through said conduit to said body;

a variable permeability membrane capable of adjusting the rate at which the volume of said media is increased; and means for controlling the the permiability of said variable permiability membrane, whereby the rate of delivery of said treatment agent may be adjusted.

2. A device, as claimed in claim 1, wherein said treatment agent comprises a drug.

3. A device, as claimed in claim 1, wherein said variable permeability membrane is for controlling the rate at which said body fluid enters said second chamber.

4. A device, as claimed in claim 1, wherein said means for applying pressure comprises a plastic impermeable sheet that changes shape depending on the volume of said media in said second chamber.

5. A device, as claimed in claim 1, wherein said increase in volume of said media is due to osmosis.

6. A device, as claimed in claim 1, wherein said membrane comprises a liquid crystalline membrane.

7. A device, as claimed in claim 6, wherein said membrane comprises a porous structure containing a polymeric liquid crystal which can undergo a phase change.

8. A device, as claimed in claim 1, wherein said means for controlling utilizes an electric field.

9. A device, as claimed in claim 1, wherein said means for controlling utilizes a magnetic field.

10. A device, as claimed in claim 1, and further comprising a semipermeable membrane located between said variable permeability membrane and said second chamber.

11. A device, as claimed in claim 1, wherein said means for controlling comprises a power supply for controlling the voltage applied to said variable permeability membrane.

12. A device, as claimed in claim 11, wherein said means for controlling further comprises:

an antenna for receiving radio frequency signals representing data; and a control circuit for causing said power supply to control said voltage according to said data.

13. A method of delivering a treatment agent to a body including body fluid comprising the steps of:

implanting a dispensing device having a first chamber and a second chamber, said first chamber containing said treatment agent and coupled to deliver said treatment agent to said body, said second chamber containing a hygroscopic media and having a variable permeability membrane;

applying pressure to said first chamber due to an increase in volume of said media in said second chamber so that said treatment agent is delivered to said body; and controlling the rate at which the volume of said media is increased with said variable permeability membrane;

whereby the rate of delivery of said treatment agent may be adjusted.

14. A method, as claimed in claim 13, wherein said step of controlling the rate is achieved using a variable permiability membrane.

15. A method, as claimed in claim 14, wherein said variable permiability membrane comprises a liquid crystalline membrane.

16. A method, as claimed in claim 14, wherein said variable permiability membrane comprises a porous structure containing a polymeric liquid crystal which can undergo a phase change.

17. A method, as claimed in claim 13, wherein said step of applying pressure is achieved using a plastic impermeable sheet that changes shape depending on the volume of said media in said second chamber.

18. A method, as claimed in claim 14, wherein said step of controlling includes the step of applying an electromagnetic parameter to said variable permiability membrane.

19. A method, as claimed in claim 18, wherein said electromagnetic parameter is an electric field.

20. A method, as claimed in claim 18, wherein said electro-magnetic parameter is a magnetic field.

21. A method, as claimed in claim 14, wherein said step of controlling the rate is achieved using a semipermeable membrane located between said variable permiability membrane and said second chamber.

22. A method, as claimed in claim 14, wherein said step of controlling is achieved using a power supply for controlling the voltage applied to said variable permiability membrane.

23. A method, as claimed in claim 22, wherein said step of controlling is achieved using an antenna for receiving data signals and a control circuit for causing said power supply to control said voltage according to said data signals.

24. An implantable dispensing device for delivering a treatment agent to a body including body fluid comprising in combination:

a first chamber for holding said treatment agent;

a conduit between said first chamber and said body;

a second chamber for holding a hygroscopic media;

means for applying pressure to said first chamber due to an increase in volume of said media in said second chamber so that said treatment agent is delivered through said conduit to said body;

a power source generating an electromagnetic parameter;

a variable permeability membrane responsive to changes in said electro-magnetic parameter for controlling the rate at which the volume of said media is increased; and means for controlling the value of said electromagnetic parameter, whereby the rate of delivery of said treatment agent is controlled.

* * * * *

UNITED STATES PATENT AND TRADEMARK OFFICE
CERTIFICATE OF CORRECTION

PATENT NO. : 5,869,078
DATED : February 9, 1999
INVENTOR(S) : Mike Baudino

It is certified that error appears in the above-identified patent and that said Letters Patent is hereby corrected as shown below:

Column 3, Line 34, Amendment 4-25-96, Page 2, Line 5: "the the" should be "the"
Column 4, Line 31, Amendment 4-25-96, Page 3, Line 15: "electromagnetic" should be "electro-magnetic"
Column 4, Line 34, Amendment 4-25-96, Page 4, Line 1: "electromagnetic" should be "electro-magnetic"
Column 4, Line 58, Amendment 4-25-96, Page 5, Line 4: "electromagnetic" should be "electro-magnetic"
Column 4, Line 63, Amendment 4-25-96, Page 5, Line 7: "electromagnetic" should be "electro-magnetic"

Signed and Sealed this

Sixth Day of June, 2000

Q. TODD DICKINSON

*Attest:*

*Attesting Officer*      *Director of Patents and Trademarks*